United States Patent [19]
Sirrenberg et al.

[11] 4,140,792
[45] Feb. 20, 1979

[54] COMBATING ARTHROPODS WITH 1-(SUBSTITUTED-PHENYLCARBAMOYL)-3-HALOPHENYL-2-PYRAZOLINES

[75] Inventors: Wilhelm Sirrenberg, Sprockhoevel; Erich Klauke, Odenthal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 861,042

[22] Filed: Dec. 15, 1977

[30] Foreign Application Priority Data

Jan. 5, 1977 [DE] Fed. Rep. of Germany ....... 2700289

[51] Int. Cl.² ...................... A01N 9/22; C07D 231/06
[52] U.S. Cl. .................................. 424/273 P; 548/379
[58] Field of Search ...................... 548/379; 424/273 P

[56] References Cited

U.S. PATENT DOCUMENTS

| 3,991,073 | 11/1976 | Mulder et al. | 424/248.5 |
| 4,010,271 | 3/1977 | Mulder et al. | 424/273 P |
| 4,070,365 | 1/1978 | van Daalen et al. | 424/273 P |

OTHER PUBLICATIONS

Philips, Chem. Absts., 1975, vol. 82, No. 43411v.
Weber et al., "Chem. Abst.", 1972, vol. 77, No. 101452u.

Primary Examiner—Natalie Trousof
Assistant Examiner—Natalia Harkaway
Attorney, Agent, or Firm—Sprung, Felfe, Horn, Lynch & Kramer

[57] ABSTRACT 1-(Substituted-phenylcarbamoyl)-3-halophenyl-2-pyrazolines of the forumla

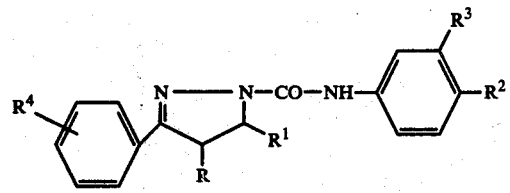

in which
R represents hydrogen or alkyl,
$R^1$ represents hydrogen or halogenophenyl,
$R^2$ represents hydrogen, halogenoalkoxy or halogenoalkylthio,
$R^3$ represents hydrogen, halogen, halogenoalkoxy or halogenoalkylthio and
$R^4$ represents halogen,
with the proviso that one of the radicals $R^2$ and $R^3$ must represent halogenoalkoxy or halogenoalkylthio, which possess arthropodicidal properties.

10 Claims, No Drawings

COMBATING ARTHROPODS WITH 1-(SUBSTITUTED-PHENYLCARBAMOYL)-3-HALOPHENYL-2-PYRAZOLINES

The present invention relates to and has for its objects the provision of particular new 1-(substituted-phenylcarbamoyl)-3-halophenyl-2-pyrazolines which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is already known that chlorophenylcarbamoyl-2-pyrazolines, for example 1-(4-chlorophenylcarbamoyl)-3-(4-chlorophenyl)-5-methyl- or 1-(4-chlorophenylcarbamoyl)-3,5-bis-(4-chlorophenyl)-2-pyrazoline, are distinguished by an insecticidal activity (see German Offenlegungsschriften (German Published Specifications) 2,304,584 and 2,529,689).

The present invention now provides, as new compounds, the substituted phenylcarbamoyl-2-pyrazolines of the general formula

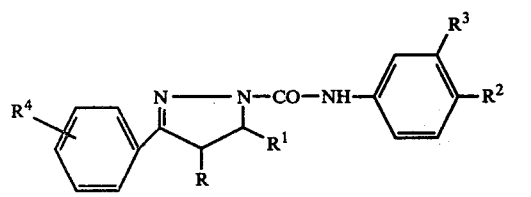

in which
R represents hydrogen or alkyl,
$R^1$ represents hydrogen or halogenophenyl,
$R^2$ represents hydrogen, halogenoalkoxy or halogenoalkylthio,
$R^3$ represents hydrogen, halogen, halogenoalkoxy or halogenoalkylthio and
$R^4$ represents halogen, with the proviso that one of the radicals $R^2$ and $R^3$ must represent halogenoalkoxy or halogenoalkylthio.

Preferably, R represents hydrogen or straight-chain or branched alkyl with 1 to 3 carbon atoms (especially methyl), $R^1$ represents hydrogen or phenyl which carries one or more substituents selected independently from chlorine and bromine atoms, $R^2$ represents hydrogen or halogenoalkoxy or halogenoalkylthio with 1 to 3 carbon atoms (especially monofluoro-, difluoro-, trifluoro-, monochlorodifluoro-, dichloromonofluoro- and monochloromonofluoro-methoxy or -methylthio, or 1,1,2,2-tetrafluoroethoxy or -ethylthio), $R^3$ represents hydrogen, chlorine, bromine or halogenoalkoxy or halogenoalkylthio with 1 to 3 carbon atoms and $R^4$ represents chlorine or bromine.

Surprisingly, the substituted phenylcarbamoyl-2-pyrazolines according to the invention exhibit a better insecticidal action than the known chlorophenylcarbamoyl-2-pyrazolines of analogous structure and of the same type of action. The products according to the present invention thus represent a genuine enrichment of the art.

The invention also provides a process for the preparation of a substituted phenylcarbamoyl-2-pyrazoline of the formula (I) in which a 2-pyrazoline of the general formula

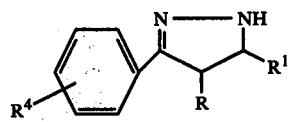

in which
R, $R^1$ and $R^4$ have the above-mentioned meanings, is reacted with a phenyl isocyanate of the general formula

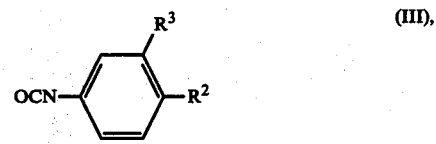

in which
$R^2$ and $R^3$ have the above-mentioned meanings, if appropriate in the presence of a diluent or solvent.

If, for example, 3-(4-chlorophenyl)-2-pyrazoline and 3-monochlorodifluoromethoxy-4-chlorophenyl isocyanate are used as starting materials, the course of the reaction can be represented by the following equation:

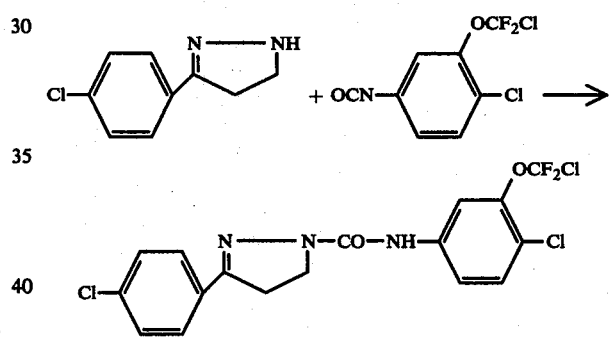

The 2-pyrazolines of the formula (II) to be used as starting materials are known and can be prepared in accordance with processes known from the literature (see, for example, German Offenlegungsschriften (German Published Specifications) 2,304,584 and 2,529,689).

The following may be mentioned as individual examples of these compounds: 3-(4-chlorophenyl)-2-pyrazoline, 3-(4-bromophenyl)-2-pyrazoline, 3-(3-chlorophenyl)-2-pyrazoline, 3-(3-bromophenyl)-2-pyrazoline, 3-(4-chlorophenyl)-4-methyl-2-pyrazoline, 3-(4-bromophenyl)-4-methyl-2-pyrazoline, 3-(3-chlorophenyl)-4-methyl-2-pyrazoline, 3-(3-bromophenyl)-4-methyl-2-pyrazoline, 3,5-bis-(4-chlorophenyl-2-pyrazoline, 3,5-bis-(4-bromophenyl)-2-pyrazoline, 3,5-bis-(3-chlorophenyl-2-pyrazoline and 3,5-bis-(3-bromophenyl)-2-pyrazoline.

The phenyl isocyanates of the formula (III) to be used as starting compounds are known and can be prepared in accordance with processes known from the literature, for example from the corresponding anilines, by means of phosgene (see Belgian Pat. Specification No. 746,566).

The following may be mentioned as individual examples of these compounds: 3-monofluoromethoxy-phenyl isocyanate, 3-difluoromethoxy-phenyl isocyanate, 3-trifluoromethoxyphenyl isocyanate, 3-monochloromonofluoromethoxy-phenyl isocyanate, 3-dichloromonofluoromethoxy-phenyl isocyanate, 3-monochlorodifluoromethoxy-phenyl isocyanate, 3-(1,1,2,2-tetrafluoroethoxy)-phenyl isocyanate, 3-monofluoromethylthio-phenyl isocyanate, 3-difluoromethylthio-phenyl isocyanate, 3-trifluoromethylthiophenyl isocyanate, 3-monochloromonofluoromethylthio-phenyl isocyanate, 3-dichloromonofluoromethylthio-phenyl isocyanate, 3-monochlorodifluoromethylthiophenyl isocyanate, 3-(1,1,2,2-tetrafluoroethylthio)-phenyl isocyanate, 4-monofluoromethoxy-phenyl isocyanate, 4-difluoromethoxy-phenyl isocyanate, 4-trifluoromethoxy-phenyl isocyanate, 4-monochloromonofluoromethoxy-phenyl isocyanate, 4-dichloromonofluoromethoxy-phenyl isocyanate, 4-monochlorodifluoromethoxy-phenyl isocyanate, 4-(1,1,2,2-tetrafluoroethoxy)-phenyl isocyanate, 4-monofluoromethylthio-phenyl isocyanate, 4-difluoromethylthio-phenyl isocyanate, 4-trifluoromethylthio-phenyl isocyanate, 4-monochlorofluoromethylthio-phenyl isocyanate, 4-dichloromonofluoromethylthio-phenyl isocyanate, 4-monochlorodifluoromethylthio-phenyl isocyanate, 4-(1,1,2,2-tetrafluoroethylthio)-phenyl isocyanate, 3-chloro-4-monofluoromethoxy-phenyl isocyanate, 3-chloro-4-difluoromethoxy-phenyl isocyanate, 3-chloro-4-trifluoromethoxy-phenyl isocyanate, 3-chloro-4-monochloromonofluoromethoxy-phenyl isocyanate, 3-chloro-4-dichloromonofluoromethyoxy-phenyl isocyanate, 3-chloro-4-monochlorodifluoromethoxy-phenyl isocyanate, 3-chloro-4-(1,1,2,2-tetrafluoroethoxy)-phenyl isocyanate, 3-bromo-4-monofluoromethoxy-phenyl isocyanate, 3-bromo-4-difluoromethoxy-phenyl isocyanate, 3-bromo-4-trifluoromethoxy-phenyl isocyanate, 3-bromo-4-monochloromonofluoromethoxy-phenyl isocyanate, 3-bromo-4-dichloromonofluoromethoxy-phenyl isocyanate, 3-bromo-4-monochlorodifluoromethoxy-phenyl isocyanate, 3-bromo-4-(1,1,2,2-tetrafluoroethoxy)-phenyl isocyanate, 3-chloro-4-monofluoromethylthio-phenyl isocyanate, 3-chloro-4-difluoromethylthiophenyl isocyanate, 3-chloro-4-trifluoromethylthio-phenyl isocyanate, 3-chloro-4-monochloromonofluoromethylthio-phenyl isocyanate, 3-chloro-4-dichloromonofluoromethylthio-phenyl isocyanate, 3-chloro-4-monochlorodifluoromethylthio-phenyl isocyanate, 3-chloro-4-(1,1,2,2-tetrafluoroethylthio)-phenyl isocyanate, 3-bromo-4-monofluoromethylthio-phenyl isocyanate, 3-bromo-4-difluoromethylthio-phenyl isocyanate, 3-bromo-4-trifluoromethylthio-phenyl isocyanate, 3-bromo-4-monochloromonofluoromethylthio-phenyl isocyanate, 3-bromo-4-dichloromonofluoromethylthio-phenyl isocyanate, 3-bromo-4-monochlorodifluoromethylthio-phenyl isocyanate and 3-bromo-4-(1,1,2,2-tetrafluoroethylthio)-phenyl isocyanate.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature can be varied within a substantial range. In general, the reaction is carried out at from 20° to 120° C., preferably at from 50° to 90° C.

In general, the reaction is allowed to take place under normal pressure.

To carry out the process, the starting components are in most cases employed in stoichiometric amounts. An excess of one or other reactant produces no significant advantages. In most cases, the reactants are brought together in one of the above-mentioned solvents and are stirred at an elevated temperature for one or more hours to complete the reaction, the reaction solution is cooled and the compound which precipitates is filtered off. The compounds are obtained in a crystalline form and are characterized by their melting point.

As already mentioned, the substituted phenylcarbamoyl-2-pyrazolines according to the invention are distinguished by an excellent insecticidal action. They are active against plant pests and, in the veterinary medicine field, against ectoparasites, such as parasitic fly larvae. Some of the compounds also exhibit fungicidal and bactericidal actions.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migrazoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosi-*

*phum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicially effective amount, of the particular active compound of the invention alone or together with a carrier vehicle as noted above. The instant formulations or compositions are applied to the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

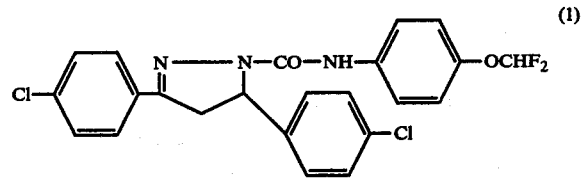

(1)

5.55 g (0.03 mol) of 4-difluoromethoxy-phenyl isocyanate in 20 ml of toluene were added, at 50° C., to a solution of 8.74 g (0.03 mol) of 3-(4-chlorophenyl)-5-(4-chlorophenyl)-2-pyrazoline in 100 ml of toluene and the batch was stirred for 2 hours at 80° C. After it had cooled, the product which had precipitated was isolated by filtration. 5 g (35% of theory) of 1-(4-difluoromethoxyphenylcarbamoyl)-3-(4-chlorophenyl)-5-(4-chlorophenyl)-2-pyrazoline of melting point 174° C. were obtained.

EXAMPLE 2

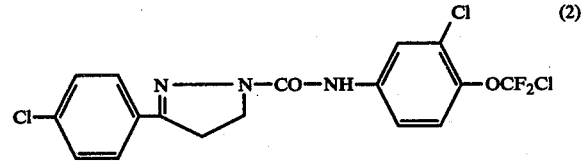

(2)

12.7 g (0.05 mol) of 3-chloro-4-monochlorodifluoromethoxy-phenyl isocyanate in 20 ml of toluene were added, at 60° C., to a solution of 9 g (0.05 mol) of 3-(4-chlorophenyl)-2-pyrazoline in 60 ml of toluene. The batch was stirred for 2 hours at 80° C. On cooling to room temperature, the product precipitated and was filtered off. 8.5 g (39% of theory) of 1-[(3-chloro-4-monochlorodifluoromethoxy-phenyl)-carbamoyl]-3-(4-chlorophenyl)-2-pyrazoline with a melting point of 161° C. were obtained.

The following compounds were synthesised analogously; The yields were not optimized:

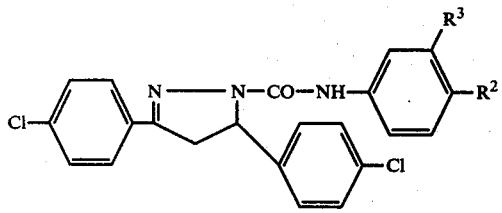

(Ia)

Table 1

| Compound No. | R² | R³ | Melting point °C |
| --- | --- | --- | --- |
| 3 | OCF₂Cl | Cl | 161 |
| 4 | SCF₂Cl | Cl | 165 |
| 5 | OCF₃ | Cl | 173 |
| 6 | H | SCF₃ | 173 |
| 7 | H | OCF₃ | 177 |
| 8 | SCF₃ | H | 160 |
| 9 | SCF₃ | Cl | 193 |
| 10 | OCF₃ | H | 180 |

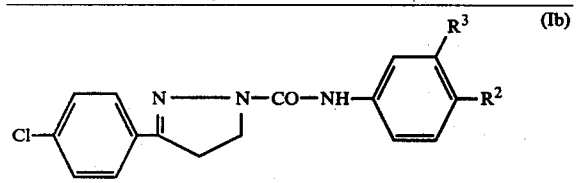

(Ib)

Table 2

| Compound No. | R² | R³ | Melting point °C |
| --- | --- | --- | --- |
| 11 | OCHF₂ | H | 150.5 |
| 12 | SCF₂Cl | Cl | 180 |
| 13 | OCF₃ | H | 127 |
| 14 | H | OCF₃ | 128 |
| 15 | H | SCF₃ | 155 |
| 16 | SCF₃ | H | 155 |
| 17 | OCF₃ | Cl | 176 |
| 18 | SCF₃ | Cl | 178 |
| 19 | OCHF₂ | Cl | 174 |
| 20 | OCF₂—CHF₂ | H | 134 |

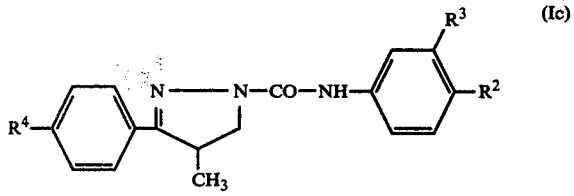

(Ic)

Table 3

| Compound No. | R² | R³ | R⁴ | Melting point °C |
| --- | --- | --- | --- | --- |
| 21 | OCF₂Cl | Cl | Cl | 127 |
| 22 | OCHF₂ | H | Cl | 130–131 |
| 23 | SCF₂Cl | Cl | Cl | 158 |
| 24 | OCHF₂ | H | Br | 137–138 |
| 25 | OCF₃ | H | Br | 159 |
| 26 | H | SCF₃ | Br | 140–141 |
| 27 | SCF₂Cl | Cl | Br | 173.5 |
| 28 | OCF₂—CF₂H | H | Br | 187.5 |
| 29 | SCF₃ | Cl | Br | 151.5 |
| 30 | OCHF₂ | Cl | Br | 150 |

The insecticidal activity of the compounds of this invention is illustrated by the following examples wherein the compounds according to the present invention are each identified by the number (given in brackets) from the preparative examples hereinabove.

The known comparison compounds are identified as follows:

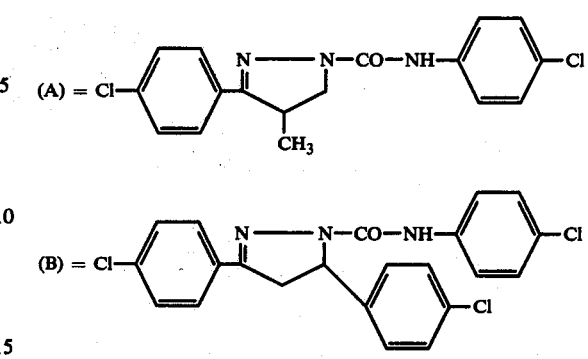

EXAMPLE 3

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 4

| | (Insects which damage plants) Phaedon larvae test | |
| --- | --- | --- |
| Active compounds | Active compound concentration in % | Degree of destruction in % after 4 days |
| (A) | 0.01 | 100 |
| | 0.001 | 0 |
| (B) | 0.01 | 100 |
| | 0.001 | 0 |
| (13) | 0.01 | 100 |
| | 0.001 | 100 |
| (17) | 0.01 | 100 |
| | 0.001 | 100 |
| (11) | 0.01 | 100 |
| | 0.001 | 100 |
| (2) | 0.01 | 100 |
| | 0.001 | 95 |

EXAMPLE 4

Laphygma test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dewmoist and were then infested with caterpillars of the owlet moth (*Laphygma exigua*).

After the specified periods of time, the destruction in % was determined. 100% meant that all of the caterpillars had been killed whereas 0% indicated that none of the caterpillars had been killed.

The active compounds, the concentrations of the active compounds, the evaluation times and the results can be seen from the following table:

Table 5

| | (Insects which damage plants) *Laphygma* test | |
|---|---|---|
| Active compounds | Active compound concentration in % | Degree of destruction in % after 4 days |
| (B) | 0.1 | 100 |
| | 0.01 | 80 |
| | 0.001 | 0 |
| (20) | 0.1 | 100 |
| | 0.01 | 100 |
| | 0.001 | 100 |
| (22) | 0.1 | 100 |
| | 0.01 | 100 |
| | 0.001 | 70 |
| (24) | 0.1 | 100 |
| | 0.01 | 100 |
| | 0.001 | 100 |
| (21) | 0.1 | 100 |
| | 0.01 | 100 |
| | 0.001 | 100 |
| (29) | 0.1 | 100 |
| | 0.01 | 100 |
| | 0.001 | 80 |
| (25) | 0.1 | 100 |
| | 0.01 | 100 |
| | 0.001 | 100 |

EXAMPLE 5

Test with parasitic fly larvae
Emulsifier: 80 parts by weight of castor oil polyglycol ether To produce a suitable preparation of active compound, 20 parts by weight of the active compound were mixed with the stated amount of the emulsifier and the mixture thus obtained was diluted with water to the desired concentration.

About 20 fly larvae (*Lucilia cuprina*, resistant) were introduced into a test tube which contained about 3 ml of a 20% strength suspension of egg-yolk-powder in water, and which was fitted with cottonwool plugs of appropriate size. 0.5 ml of the active compound preparation was placed on this egg-yolk-powder suspension. After 24 hours, the degree of destruction in % was determined. 100% meant that all of the larvae had been killed and 0% than none of the larvae had been killed.

The active compounds, active compound concentrations and results can be seen from the table which follows:

Table 6

| | Test with parasitic fly larvae | |
|---|---|---|
| Active compound | Active compound concentration in ppm | Destructive action in % |
| (13) | 1,000 | 100 |
| | 300 | 100 |
| | 100 | 100 |
| (16) | 1,000 | 100 |
| | 300 | 100 |
| | 100 | 100 |
| (25) | 1,000 | 100 |
| | 100 | 100 |
| (20) | 1,000 | 100 |
| | 300 | 100 |
| | 100 | 100 |

It will be appreciated that the instant specification and examples are set forth by way of illustration and not limitation, and that various modifications and changes may be made without departing from the spirit and scope of the present invention.

What is claimed is:

1. A 1-(substituted-phenylcarbamoyl)-3-halophenyl-2-pyrazoline of the formula

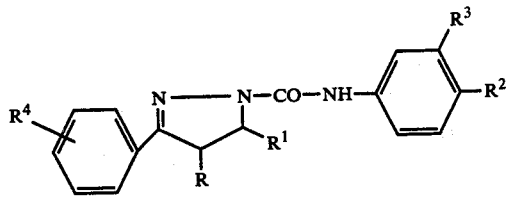

in which
R represents hydrogen or alkyl with 1 to 3 carbon atoms,
$R^1$ represents hydrogen or halogenophenyl,
$R^2$ represents hydrogen, or halogenoalkoxy or halogenoalkylthio with 1 to 3 carbon atoms,
$R^3$ represents hydrogen, halogen, or halogenoalkoxy or halogenoalkylthio with 1 to 3 carbon atoms and
$R^4$ represents halogen, with the proviso that one of the radicals $R^2$ and $R^3$ must represent halogenoalkoxy or halogenoalkylthio.

2. A compound according to claim 1, in which
$R^1$ is hydrogen or phenyl carrying at least one chlorine or bromine atom,
$R^3$ is hydrogen, chlorine, bromine or halogenoalkoxy or halogenoalkylthio with 1 to 3 carbon atoms, and
$R^4$ is chlorine or bromine.

3. A compound according to claim 1, wherein such compound is 1-[(3-chloro-4-monochlorodifluoromethoxy-phenyl)-carbamoyl]-3-(4-chlorophenyl)-2-pyrazoline of the formula

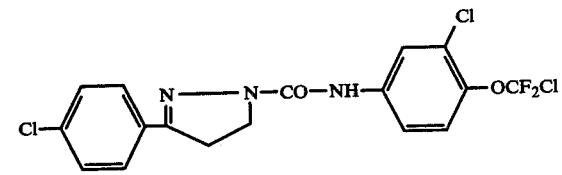

4. A compound according to claim 1, wherein such compound is 1-[(4-difluoromethoxy-phenyl)-carbamoyl]-3-(4-chlorophenyl)-2-pyrazoline of the formula

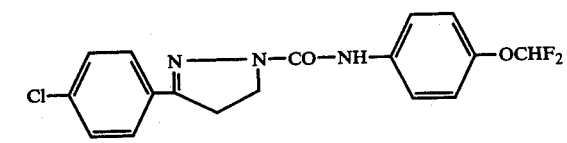

5. A compound according to claim 1, wherein such compound is 1-[(4-trifluoromethoxy-phenyl)-carbamoyl]-3-(4-chlorophenyl)-2-pyrazoline of the formula

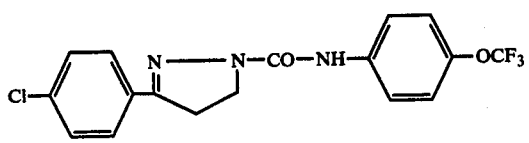

6. A compound according to claim 1, wherein such compound is 1-[(3-chloro-4-trifluoromethoxy-phenyl)-carbamoyl]-3-(4-chlorophenyl)-2-pyrazoline of the formula

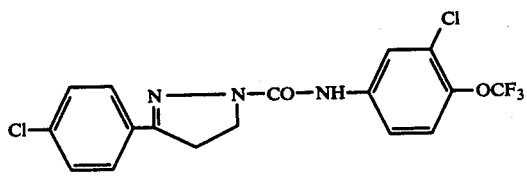

7. A compound according to claim 1, wherein such compound is 1-{[4-(1,1,2,2-tetrafluoroethyl)-phenyl]-carbamoyl}-3-(4-chlorophenyl)-2-pyrazoline of the formula

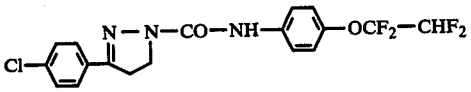

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method of freeing or protecting domesticated animals from ectoparasitical insects which comprises applying to said animals an ectoparasiticidally effective amount of
1-[(3-chloro-4-monochlorodifluoromethoxyphenyl)-carbamoyl]-3-(4-chlorophenyl)-2-pyrazoline,
1-[(4-difluoromethoxy-phenyl)-carbamoyl]-3-(4-chlorophenyl)-2-pyrazoline,
1-[(4-trifluoromethoxy-phenyl)-carbamoyl]-3-(4-chlorophenyl)-2-pyrazoline,
1-[(3-chloro-4-trifluoromethoxy-phenyl)-carbamoyl]-3-(4-chlorophenyl)-2-pyrazoline, or
1-{[4-(1,1,2,2-tetrafluoroethyl)-phenyl]-carbamoyl}-3-(4-chlorophenyl)-2-pyrazoline.

* * * * *